United States Patent [19]
Kinnersley

[11] Patent Number: 6,124,241
[45] Date of Patent: Sep. 26, 2000

[54] METHOD FOR INCREASING PLANT PRODUCTIVITY USING GLUTAMIC ACID AND GLYCOLIC ACID

[75] Inventor: Alan M. Kinnersley, East Lansing, Mich.

[73] Assignee: Auxien Corporation, Lansing, Mich.

[21] Appl. No.: 09/182,140

[22] Filed: Oct. 29, 1998

[51] Int. Cl.[7] ............................ A01N 37/36; A01N 37/44
[52] U.S. Cl. ............................................................ 504/147
[58] Field of Search ............................................. 504/147

[56] References Cited

U.S. PATENT DOCUMENTS

| | | | |
|---|---|---|---|
| 3,679,392 | 7/1972 | Strauss et al. | 71/89 |
| 4,491,464 | 1/1985 | Ashmead et al. | 71/11 |
| 4,813,997 | 3/1989 | Kinnersley et al. | 71/66 |
| 4,908,353 | 3/1990 | Yamamoto et al. | 514/19 |
| 5,439,873 | 8/1995 | Kinnersley | 504/158 |
| 5,593,947 | 1/1997 | Kinnersley et al. | 504/283 |
| 5,597,400 | 1/1997 | Nonomura et al. | 71/28 |
| 5,604,177 | 2/1997 | Kinnersley et al. | 504/147 |
| 5,814,582 | 9/1998 | Koskan et al. | 504/320 |
| 5,840,656 | 11/1998 | Kinnersley et al. | 504/115 |
| 6,008,256 | 12/1999 | Haraguchi et al. | 514/626 |

FOREIGN PATENT DOCUMENTS

| | | |
|---|---|---|
| 0 208 403 A1 | 5/1986 | European Pat. Off. . |
| WO 98/00012 | 1/1998 | WIPO . |

OTHER PUBLICATIONS

M. Santos, I. Claparols & J.M. Torne; "Effect of Exogenous Arginine, Ornithine, Methionine and GABA on Maize (*Zea Mays* L.) Embryogenesis and Polyamine Content," J. Plant Physiol., vol. 142, 1993, pp. 74–80, XP002075993.

Derwent Publications Ltd., AN 81–63554D, XP002075994 and JP 56032961B (Ajinomoto KK) (Abstract).

Chemical Abstracts 74:95454r (1971).

CABA Abstract 73:30077 (1973).

WPIDS Abstract 85–084635 (1985).

Chemical Abstract 93:235305n (1980).

Chemical Abstract 116:20002u (1991).

Chemical Abstract 99:36050z (1983).

SOLU–SPRAY Pamphlet by: Leffingwell Chemical Company, 1987.

"The Production and Efflux of 4–Aminobutyrate in Isolated Mesophyll Cells[1]," Induk Chung, Alan W. Brown & Barry J. Shelp. *Plant Physiol*. 99:659–664, 1992.

"Comptes Rendus—Des Seances—De L'Academie Des Sciences; Physiologie Vegetale." *C.R.Acad.Sc.Paris*, t.271, Series D, pp. 2316–2319 (1970).

"Metabolism, Enzymology & Possible Roles of 4–Aminobutyrate in Higher Plants" (Review Article No. 51); V. Satya Narayan and P.M. Nair, *Phytochemistry*, 29:367–375, 1990.

"The Metabolism and Functions of γ–Aminobutyric Acid," Alan W. Brown and Barry J. Shelp. *Plant Physiol*.115:1–5, 1997.

(List continued on next page.)

*Primary Examiner*—S. Mark Clardy
*Attorney, Agent, or Firm*—Woodard, Emhardt, Naughton Moriarty & McNett

[57] ABSTRACT

Compositions including glutamic acid and either glycolic acid or polyglycolic acid are described as are such compositions that include a calcium salt, preferably calcium nitrate. Methods of treating a plant including treating the plant or seed with a composition including glutamic acid and either glycolic acid or polyglycolic acid are also described. Methods of treating a plant including treating the plant or seed with a composition that includes glutamic acid, a calcium salt and either glycolic acid or polyglycolic acid are also described. The methods and compositions of the present invention are advantageous in increasing plant productivity, including helping plants resist environmental stresses.

45 Claims, 5 Drawing Sheets

OTHER PUBLICATIONS

"Glycolate and glyoxylate stimulation of growth in *Lemna gibba*," Elisabeth Tillberg. *Physiol.Plant* 50:158–160, 1980.

"Effect of Low–Molecular–Weight Organic Acids of Peat Soil on the Growth of Barley Plants," V.I. Terent'ev, R.I. Tsareva, and O.V. Shchutskaya. Institute of Experimental Botany and Microbiology Belorussian Academy of Sciences; The Belorussian Affiliate of the All–Union Botanic Society; Physiological and Biochemical Study of Plants. Minsk, 1965.

"On the Content of Organic Acids in Peat Soil and Their Effect on the Growth of Barley," Translated from Physiological Features of Cultivated Plants, Institute of Experimental Botany and Microbiology of he Academy of Sciences of the Byelorussian SSR, Byelorussian Division of the All–Union Botanical Society, Izd. Nauka I Tekhnika, Minsk, 1964.

"Nitrogen Metabolism in Plant Cell Suspension Cultures," Josef Behrend and Richard I. Mateles. *Plant Physiol.* 56:584–589, 1975.

METHOD FOR INCREASING PLANT PRODUCTIVITY USING GLUTAMIC ACID AND GLYCOLIC ACID

FIELD OF THE INVENTION

The present invention relates generally to a process for increasing plant productivity. Specifically, the method relates to increasing plant productivity by treating roots, seeds, stems and/or foliage of plants with compositions containing glutamic acid and either polyglycolic acid or glycolic acid.

BACKGROUND OF THE INVENTION

Many organic acids and amino acids, including glutamic acid and glycolic acid, are useful for stimulating plant growth. For example, in 1980, Tillberg (*Physiol. Plant* 50:158–160) reported that duckweed growth was stimulated by 10 to 20% when low levels of glycolic acid (30–220 ppm) were added to culture media, although levels of 380 ppm or higher were inhibitory to growth.

Oligomers of glycolic acid which are hydrolyzed to monomers have also been reported to stimulate duckweed growth (Kinnersley et al., U.S. Pat. No. 4,813,997). Behrend & Meteles (1975, *Plant Physiol.* 56:584–589) found that glutamic acid increased the growth of cell cultures of tobacco, tomato, and carrot, however, the effects of this amino acid on intact plants are less clear. Gorham (1950, *Canadian J. of Research* 28:356–381) found that glutamic acid (100 ppm) had negative effects on plant growth.

While increasing vegetative plant growth is important, of much greater significance is stimulation of reproductive growth that gives increased yield of fruits, vegetables, grains, etc. Compositions of organic acids that increase plant productivity, and in particular that increase reproductive growth, are therefore needed. The present invention addresses this need.

SUMMARY OF THE INVENTION

In one aspect of the invention, a method of treating a plant with a composition comprising glutamic acid and glycolic acid is provided. The method is advantageous in increasing plant productivity, including increasing the growth of plants, increasing the ripeness of the fruit of plants and increasing the resistance of the plants to disease and other stresses.

In another aspect of the invention, a method of treating a plant comprising treating the plant with a composition comprising glutamic acid and glycolic acid in amounts effective in increasing plant productivity is provided.

In yet another aspect of the invention, a method of treating a plant with a composition comprising glutamic acid, glycolic acid and a calcium salt is provided. The calcium salt is preferably calcium nitrate.

Another aspect of the invention relates to a method of treating a plant comprising treating the plant with a composition comprising glutamic acid and polyglycolic acid having the following formula:

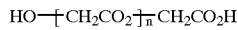

wherein n=1–10.

The composition may further comprise a calcium salt, preferably calcium nitrate.

In another embodiment of the invention, compositions comprising glutamic acid and glycolic acid are provided. The compositions are preferably present in a suitable carrier medium.

In another aspect of the invention, a composition comprising glutamic acid, glycolic acid and a calcium salt is provided.

In yet another embodiment of the invention, a composition comprising glutamic acid and polyglycolic acid having the following formula is provided:

wherein n=1–10.

It is an object of the invention to provide a method for treating a plant that will increase plant productivity.

It is a further object of the invention to provide a composition with properties conducive for increasing plant productivity.

Further objects and advantages of the present invention will be apparent from the following description.

DESCRIPTION OF THE PREFERRED EMBODIMENT

Figure 1:
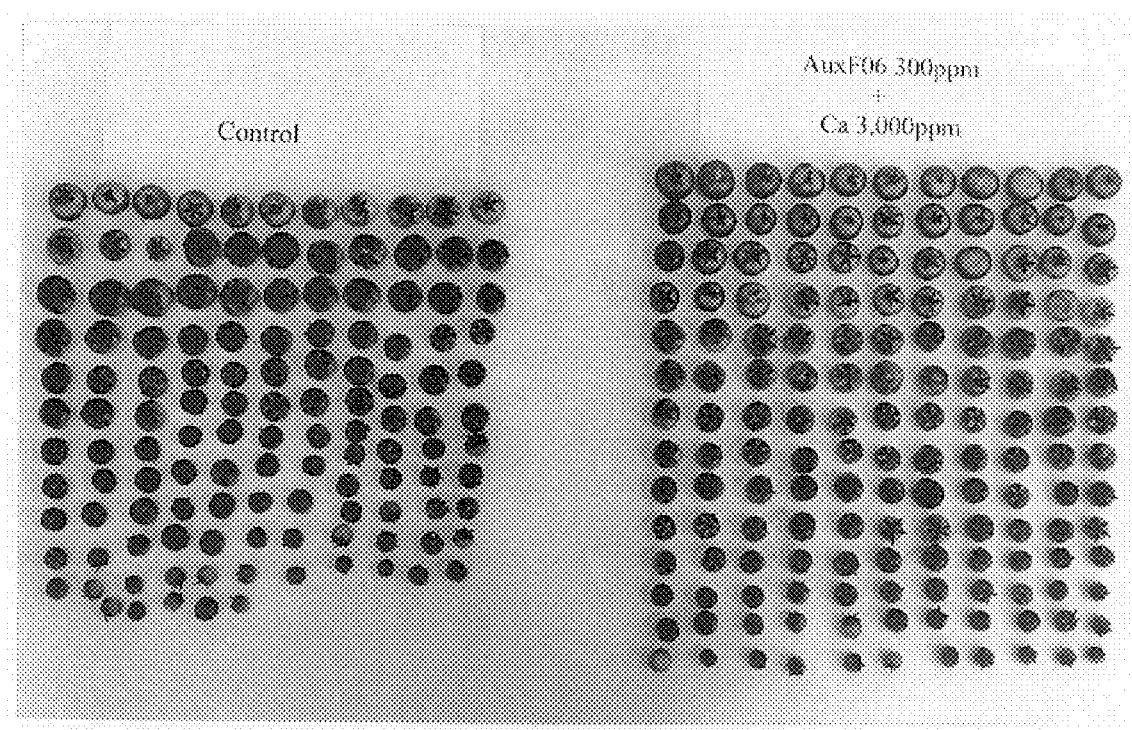
FIG. 1 depicts the effect of AuxF06 (a glutamic acid and glycolic acid composition) in combination with calcium nitrate on the yield of Tiny Tim tomatoes. Left panel: tomatoes from control plants; Right panel: tomatoes from plants treated with 300 ppm AuxF06 and 3000 ppm calcium nitrate.

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention relates to a composition comprising glutamic acid and either glycolic acid or polyglycolic acid. The polyglycolic acid has the following formula:

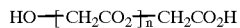

wherein n=1–10.

The composition of the present invention has properties conducive for increasing plant productivity. For example, by combining glutamic acid and either glycolic acid or polyglycolic acid, an unexpected greater stimulation of plant growth occurs than is possible using either acid alone. The compositions are also very effective at increasing reproductive plant growth, increasing the ripening of fruit, the germination of seeds, and protecting plants from disease and other stresses. The compositions may thus allow for earlier harvesting of harvestable produce. Optionally, calcium salts are included and enhance the efficacy of the plant treatments.

In a first aspect of the invention, a composition is provided that includes glutamic acid and glycolic acid.

Glutamic acid and glycolic acid may be obtained from commercial sources or may be synthesized by methods known in the art. Glutamic acid may also be isolated from natural sources by methods known in the art. Any form of glutamic acid may be used, including various salts of glutamic acid, including the monosodium salts.

The concentrations of glutamic acid and glycolic acid in the compositions and the amount of the compositions effective in increasing plant productivity will depend on various factors, including the type of plant, the quantity of plants treated, and whether increased ripening, increased plant growth, or increased resistance to disease is desired. The desired concentrations and amounts can be determined by one skilled in the art.

Typically, compositions include about 0.5 ppm to about 5,000 ppm glycolic acid, and about 0.5 ppm to about 5,000 ppm glutamic acid, but preferably include about 0.5 ppm to about 2,500 ppm glycolic acid, and about 0.5 ppm to about 2,500 ppm glutamic acid, and more preferably, include about 50 ppm to about 500 ppm glutamic acid, and about 50 ppm to about 500 ppm glutamic acid, all on weight/volume basis. It is further preferable that the compositions be comprised of a 1:1 composition of the components. A 1:1 composition as defined herein is a composition having equal weights of the individual components or equal volumes of solutions containing a single component provided the solutions are at the same concentration.

In another aspect of the invention, a composition is provided comprising glutamic acid, glycolic acid, and a calcium salt. Any salt of calcium may be used, including chloride and sulphate. Calcium nitrate, however, is preferred. Addition of the calcium salt to a composition including glycolic acid and glutamic acid may further increase plant productivity. For example, addition of calcium nitrate to a composition comprising glutamic acid and glycolic acid increases reproductive plant growth and may increase the early ripening of harvestable produce, including fruit, to a greater extent than the same composition without calcium nitrate.

In compositions that include a calcium salt, such as calcium nitrate, the salt is typically present in amounts of about 100 ppm to about 10,000 ppm, but may vary depending on the application.

Alternatively, the composition may include glutamic acid and polymers of glycolic acid (polyglycolic acid) having the following formula:

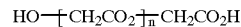

wherein n=1–10.

The composition may also include glutamic acid and a 70% aqueous solution of glycolic acid which contains low levels of oligomers wherein n=2–4.

In a related embodiment, the composition further includes a calcium salt, preferably calcium nitrate, as discussed above for the composition including glutamic acid and glycolic acid.

Polyglycolic acid may be produced by heating monomeric glycolic acid under reduced pressure at an elevated temperature as described in U.S. Pat. No. 4,813,997, which is hereby incorporated by reference. Linear condensation polymers of glycolic acid are most useful in the practice of the invention. The polymeric mixture obtained by heating monomeric glycolic acid under reduced pressure may be used without purification. However, the polymeric mixture can be separated into its components by various fractionation techniques known in the art, if desired. Moreover, small amounts of polymerized glycolic acid occur naturally in concentrated aqueous solutions of glycolic acid. The most cost effective source of glycolic acid is a 70% solution of glycolic acid, manufactured by DuPont, which contains 6–8% glycolic acid dimers.

The concentrations of glutamic acid and polyglycolic acid and the amount of the composition effective in increasing plant productivity will depend on the various factors as discussed above. Typically, compositions include about 0.5 ppm to about 5,000 ppm glutamic acid, and about 0.5 ppm to about 5,000 ppm polyglycolic acid, but preferably include about 0.5 ppm to about 2,500 ppm glutamic acid, and about 0.5 ppm to about 2,500 ppm polyglycolic acid, and more preferably include about 50 ppm to about 500 ppm glutamic acid and about 50 ppm to about 500 ppm glutamic acid. It is further preferable that the compositions be comprised of a 1:1 composition of the components. In compositions that include a salt of nitric acid, such as calcium nitrate, the salt is typically present in amounts of about 100 ppm to about 10,000 ppm.

The compositions may be combined with a carrier medium as known in the art. For example, the compositions may be in water, including distilled and tap water, a fertilizer solution, or other pesticide solution. The pesticide may be either a chemical or biological(natural) pesticide as known in the art, including fungicides, bacteriocides and anti-virals. The pesticides include antibiotics such as streptomycin and biological bacteriocides such as *Pseudomonas fluoroscens* commercialized as blight ban A506. One skilled in the art would be familiar with the various fertilizer and pesticide solutions which may be employed. However, the compositions of the present invention are most simply combined with water.

The present invention also provides a method for treating a plant comprising treating the plant with a composition including glutamic acid and either glycolic acid or polyglycolic acid.

In one aspect of the invention, a method is provided for treating the plant with a composition described above, comprising glutamic acid and glycolic acid. The composition may further include a calcium salt, such as calcium nitrate, as described above. In another aspect of the invention, a method of treating a plant with the composition described above including glutamic acid and polyglycolic acid is also provided. The composition may further include a calcium salt of nitric acid, such as calcium nitrate.

The present invention also provides a method for treating a plant comprising treating the plant with a composition including glutamic acid and either glycolic acid or polyglycolic acid, wherein the polyglycolic acid has the following formula:

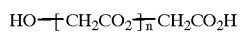

wherein n=1–10.

The composition including glutamic acid and either glycolic or polyglycolic acid (or glycolic acid and low levels of dimers of glycolic acid as discussed above), is preferably applied in amounts effective in increasing plant productivity as described above.

The method and composition of the present invention may be used to increase a plant's reproductive as well as vegetative growth. The method and composition of the present invention may be used to treat recreational plants, decorative plants, trees or crops, and is particularly useful for treating commercial crops. Examples of plants and crops that may be treated in the present invention include monocotyledons, such as duckweed, corn and turf (including rye grass, Bermuda grass, blue grass, fescue), and dicotyledons, including crucifers (such as rape seed, radishes and cabbage) and solanaceae (including green peppers, potatoes and tomatoes). The compositions of the present invention are typically applied to the roots, stems, seeds and/or foliage of the plant. When the compositions are applied, such as a foliar application, a hand sprayer may be used and the compositions are sprayed to drip. The expression "sprayed to drip" is generally defined as a volume of about 100 gallons/acre (65 l/ hectare). However, the compositions may also be applied hydroponically (as in Example 1), as a soil drench or as a seed coating.

The methods and compositions of the present invention can also be used to protect plants from disease. For example, treating plants with compositions including glutamic acid and either polyglycolic acid or glycolic acid helps plants resist infection from diseases caused by, for example, fungi (including late blight, powdery mildew disease, Pythium, Rhizoctonia and Fusarium), bacteria (including Erwinia and Pseudomonas) and viruses (including tobacco mosaic virus and squash mosaic virus).

The methods and compositions of the present invention can further be used to stimulate seed germination as shown in Examples 11, 12 and 13. For example, the methods and compositions of the present invention may increase the rate of seed germination and/or may also increase the total number of seeds which germinate.

Reference will now be made to specific examples using the processes described above. It is to be understood that the examples are provided to more completely describe preferred embodiments, and that no limitation to the scope of the invention is intended thereby.

EXAMPLE 1

Duckweed (Lemna Minor L) was grown following the general procedure described by Kinnersley (U.S. Pat. No. 5,439,873). Experiments were performed in which glycolic acid, polyglycolic acid, and glutamic acid were added to culture media separately and together and the effect on growth of duckweed was determined.

TABLE 1

| Treatments | Dry wt (mg) ± SD* | Increase in wt (mg) over control | Expected Increase in wt (mg) over control |
|---|---|---|---|
| Control | 24.3 ± 4.7 | | |
| Glutamic Acid 500 ppm | 25.2 ± 2.8 | 1.1 | |
| Glycolic Acid 1000 ppm | 31.8 ± 2.8 | 7.5 | |
| Polyglycolic Acid 1000 ppm | 35.8 ± 6.4 | 11.5 | |
| Glutamic Acid 500 ppm + Glycolic Acid 1000 ppm | 40.3 ± 4.4 | 16.2 | 8.6 |
| Glutamic Acid 500 ppm + Polyglycolic Acid 1000 ppm | 62.4 ± 6.0 | 38.1 | 12.6 |

*Standard Deviation

The results in Table 1 show that the addition of 500 ppm glutamic acid increased dry weight of duckweed by 1.1 mg over control, and that polyglycolic acid (1000 ppm) increased dry weight by 11.5 mg. From this, the addition of 500 ppm glutamic acid and 1000 ppm polyglycolic acid together to the media should increase dry weight by 12.6 mg. The actual increase, 38.1 mg, was three times greater than the expected increase. By similar reasoning, it can be seen that mixtures of glycolic acid and glutamic acid increase plant growth more than expected from the activity of the acids alone.

EXAMPLE 2

A second duckweed experiment was performed in which the effect of polyglycolic acid was examined in combination with casein hydrolysate. The casein hydrolysate was an enzymatic digest (N-Z-amine) obtained from Sigma Chemical Company, (St. Louis, MO) which contained 18.58% glutamic acid. Results of this experiment are shown in Table 2.

The media used contained 5 g/L glucose in addition to the fertilizer that was used, as described in the previous example.

TABLE 2

| Treatments | Dry wt (mg) ± SD† | Increase in weight (mg) over Control | Expected increase in weight (mg) over control |
|---|---|---|---|
| Control | 44 ± 5 | | |
| Casein Hydrolysate 500 ppm | 58 ± 3 | 14 | |
| Polyglycolic Acid 500 ppm | 59 ± 12 | 15 | |
| Casein Hydrolysate 500 ppm + Polyglycolic Acid 500 ppm | 96 ± 15 | 52 | 29 |

†Standard Deviation

Results in Table 2 show that when casein hydrolysate was added to the medium, plant growth increased as shown by the 14 mg increase in weight of the plant. Addition of polyglycolic acid increased growth as shown by the 15 mg increase in weight of the plant. Addition of casein and polyglycolic together was thus expected to cause an increase in the weight of the plant by 29 mg (i.e., 15 mg+14 mg).

However, the actual increase was 52 mg, a 79% greater than expected increase.

EXAMPLE 3

Tiny Tim tomatoes were grown in the greenhouse and treated with three foliar applications of mixtures of glutamic and glycolic acids with the first application being made at the first sign of fruit set. The second and third applications were made one week after the first application and the following week the ripe fruit from each plant was harvested. Results below show the average number of ripe fruit per plant, the average number of ripe fruit weighing more than 10 g per plant, and the total weight of ripe fruit harvested from each treatment. Each treatment and control had four replicates with three potted plants per replicate.

TABLE 3

| Treatment | # Fruit | DUN | % of Control | WT (g)* | DUN | % of NTC | Fruit Size** | DUN | % of NTC |
|---|---|---|---|---|---|---|---|---|---|
| Non Treated Control (NTC) | 1.42 | a | 100 | 13.8 | a | 100 | 7.7 | a | 100 |
| GLU/GA 100 ppm | 4.5 | bcd | 317 | 50.6 | b | 368 | 11.2 | bc | 146 |
| GLU/GA 300 ppm | 4.4 | bcd | 311 | 52.5 | b | 381 | 12.4 | c | 161 |

*the total weight of ripe fruit from each treatment
**average number of ripe fruit weighing more than 10 g.

Results in Table 3 show that mixtures of glutamic and glycolic acids [containing either 100 ppm GLU/GA (50 ppm GLU with 50 ppm GA) or 300 ppm GLU/GA (150 ppm GLU with 150 ppm GA)] increased the numbers and weight of ripe tomato fruit by more than three times when plants were given foliar applications of the acids. The numbers of large fruit were also increased in the treated plants. Duncans multiple range test was used to analyze results for statistical significance, and all the increases were found to be statistically significant as indicated by the different letters following the treatments. A letter different from the control signifies a statistical difference at a probability of 95% or greater.

A second tomato experiment was performed using a lower amount of the glutamic/glycolic acid mixture and treating 7 week-old plants with only a single application, given at the onset of fruiting. One month after the treatment was given, all the fruit on the plants was removed and weighed and results are shown below in Table 4, results being expressed as a percentage of the control.

TABLE 4

| Treatment | % of Control for Extra-Large Fruit* | DUN | % of Control for All Fruit | DUN |
|---|---|---|---|---|
| Non-treated Control (NTC) | 100 | a | 100 | a |
| GLU/GA 50 ppm | 157 | a | 111 | a |
| GLU/GA 100 ppm | 147 | a | 123 | b |

*Fruit that weighs more than 10 g.

Results show that the glutamic acid (GLU)/glycolic acid (GA) composition at 100 ppm (i.e., 50 ppm GLU with 50 ppm GA) and 50 ppm GLU/GA, (i.e., 25 ppm GLU with 25 ppm GA) increased the amount of extra large tomatoes by about 150%. Total tomato productivity was significantly increased by 123% when plants were given 100 ppm of the acid mixture. The tomato experiments show that the present invention can be used to increase early ripening of tomatoes, to increase the average size of tomatoes, and to increase total tomato yield from plants.

EXAMPLE 4

Thai hot peppers (Park Seed, Greenwood, S.C.) were grown from seed and treated with mixtures of equal parts of glutamic acid (GLU) and glycolic acid either (GA) or polyglycolic acid (PGA). Foliar treatments were given three times at weekly intervals starting at the first sign of fruit formation when plants were six weeks old. Peppers were harvested one week following the third treatment and the average number of peppers and weight of peppers for each replicate was determined.

TABLE 5

| Treatment | # Peppers/ Rep ± SD† | % Change from Control | FWT* (g) ± SD | % Change from Control |
|---|---|---|---|---|
| Control | 15.3 ± 2.9 | 100 | 25.2 ± 3.3 | 100 |
| GLU/PGA 100 ppm | 16.7 ± 1.2 | 109 | 28.2 ± 8.9 | 112 |
| GLU/PGA 300 ppm | 16.3 ± 2.5 | 107 | 25.6 ± 7.3 | 102 |
| GLU/GA 100 ppm | 16.3 ± 2.1 | 107 | 31.3 ± 2.8 | 124* |
| GLU/GA 300 ppm | 18.0 ± 4.4 | 118 | 25.4 ± 3.7 | 101 |

*Significantly different from control at 0.90.
†Standard Deviation
*Fresh weight Results show that 1:1 mixtures of glutamic acid (GLU) and glycolic acid (GA) or polyglycolic acid (PGA) increased both the number of peppers and the total weight of peppers harvested per plant. The best responses were found at the lowest level of the mixtures.

EXAMPLE 5

The procedure followed in Example 3 was repeated but in this experiment lower levels of the mixed acids were used, and harvested peppers were separated according to size. Results are shown in Table 6.

TABLE 6

|  | Control | GLU + GA 50 ppm | % Change from Control |
|---|---|---|---|
| # Large Peppers | 4.0 ± 0.9 | 7.1 ± 0.8 | 139 |
| # Total Peppers | 8.2 ± 2.4 | 12.8 ± 1.8 | 156 |
| Wt. Large Peppers | 12.9 ± 2.4 | 15.9 ± 5.1 | 124 |
| Wt. Total Peppers | 14.1 ± 2.6 | 17.5 ± 4.8 | 124 |

The data in Table 6 shows the average values and respective standard deviation from three repetitions. Each replication consisted of three plants having similar amounts of flowering.

The results in Example 5 show that low levels of the bioactive mixture (less than 1 oz active ingredients/acre—71 g/hectare) significantly increased reproductive growth, as seen by the large increases in the average numbers of peppers/plant. The increased numbers of large and total peppers were significantly different at 0.99 and 0.90 respectively.

EXAMPLE 6

Seeds of Morris cabbage (Seedway, Elizabethtown, Pa.) were germinated in 5"×5" (12.7 cm×12.7 cm) green pots containing "Bacto" potting soil. Each treatment consisted of three repetitions and each repetition included two pots with ten plants/pot. After seven days, the cabbage seedlings were sprayed with a mixture of equal parts of glutamic acid (GLU) and glycolic acid (GA) equivalent to 1 oz/acre (73.1 ml/hectare) and 2 oz/acre (146.2 ml/hectare). Two additional applications were made at two and three weeks after seeding. Plants were harvested after four weeks and fresh weights determined. The results are shown below in Table 7.

TABLE 7

| Treatment | Average Fresh Weight (g) | % Change From Control |
|---|---|---|
| Untreated Control | 26.4 ± 1.2 | 100 |
| GLU + GA 150 ppm | 30.2 ± 1.7 | 114* |
| GLU + GA 300 ppm | 29.2 ± 2.8 | 111 |

*Significantly different (p > 0.95)

EXAMPLE 7

A second experiment was performed with a different variety of cabbage (Heads-Up cabbage, Harris Seeds, Rochester, N.Y.) that was grown following the procedure described in Example 6, except that the number of cabbage plants per pot was reduced to 6. In this second experiment, the effectiveness of the composition of this invention in promoting cabbage growth was compared using liquid or solid glycolic acid in mixtures with glutamic acid. The solid glycolic acid was Glypurel, a high purity crystalline source of glycolic acid from DuPont. The liquid glycolic acid was a 70% aqueous solution of glycolic acid containing about 6–8% diglycolic acid and small amounts of larger oligomers. The liquid glycolic acid was also obtained from DuPont.

Fresh and dry weights of cabbage plants treated with different formulations are shown below in Table 8. Results show that compositions containing both liquid and solid glycolic acid increase cabbage fresh and dry weights significantly compared to controls.

TABLE 8

| Treatments | Fresh wt avg Per 6 plants | % increase from control | Dry wt avg per 12 plants | % increase from control |
|---|---|---|---|---|
| Control | 28.2 ± 2.9 | 100 | 5.1 ± .7 | 100 |
| GLU/GA (solid)† 150 ppm | 32.2 ± .8* | 114 | 6.4 ± .2** | 125 |
| GLU/GA (solid)† 300 ppm | 33.4 ± 2.1 | 118 | 6.2 ± .8 | 122 |
| GLU/GA (liq.)†† 150 ppm | 33.2 ± 1.3 | 118 | 6.9 ± .4* | 124 |
| GLU/GA (liq.)†† 300 ppm | 34.0 ± 1.3** | 121 | 6.9 ± 3** | 135 |

*Significant at 90%
**Significant at 95%
†Solid form of glycolic acid (Glypure ™ from Dupont)
††Liquid form of glycolic acid (a 70% technical solution from Dupont)

EXAMPLE 8

A third tomato experiment was performed using Tiny Tim tomatoes grown in 4" (10.2 cm) black plastic pots. Each treatment included three replicates and each replicate included three plants. Plants were given two foliar treatments one week apart with the first treatment given when plants were seven weeks old. Plants were harvested one week after the second treatment and the number and weight of ripe and unripe fruit determined. Results are shown in Table 9. FIG. 1 shows the yield of fruit taken from a single replicate of treated and untreated plants. AuxF06 is the company designation for the mixture of glutamic and glycolic acids which is the subject of the invention.

TABLE 9

| Treatment | Average Weight (g) All Fruit ± SD* | Average Weight (g) of Ripe Fruit ± SD* |
|---|---|---|
| Untreated Control | 70.0 ± 5.35 | 8.2 ± 3.8 |
| GLU + GA 300 ppm | 85.5 ± 5.3 | 23.8 ± 4.8 |
| GLU + GA 300 ppm + CaNO$_3$ 3000 ppm | 92.9 ± 4.4 | 38.0 ± 3.1 |

*Standard Deviation

Results show that mixtures of equal parts of glycolic acid (GA) and glutamic acid (GLU) increased overall tomato productivity by 21% and increased productivity of ripe fruit by 290%. Addition of 3,000 ppm CaNO$_3$ to the mixed acids significantly increased the effects.

EXAMPLE 9

Lettuce plants were used to demonstrate the value of the present invention in protecting plants from disease. Waldmann/Grand Rapids green leaf lettuce seed was sown ¼" (0.64 cm) to ½" (1.27 cm) deep in three 20" (50.8 cm) rows per flat. The flats measured 20"×10"×2" (50.8 cm×25.4 cm×5.1 cm) and were filled to the top with starter-fertilizer amended potting mix. After emergence, the seedlings were thinned to 25 plants per row (75 plants/flat). The overcrowding was intentional to increase Botrytis growth and infection. Four replicates were set up and the treatments were randomly organized. Plants were grown until nearly mature to gain row closure and sufficient senescent leaf debris for good saprophytic colonization after inoculation. The first test substance foliar treatment took place eight days prior to inoculation and the second treatment followed inoculation by eight days. Lettuce harvest occurred ten days following the second application.

Lettuce was treated with Benlate®, a fungicide, or with mixtures of glutamic acid and glycolic acid, that were given to plants as a foliar application or were left untreated. Eight days after the treatments, the lettuce was inoculated with Botrytis. Plants were given a second treatment eight days following infection and harvested ten days after the treatment. At harvest, plants were rated on a scale from 0 to 100 with 0 showing the least damage and 100 showing the most damage from fungal injection. Results of this rating are shown in Table 10.

TABLE 10

| Treatment | Disease Severity Rating |
| --- | --- |
| Non-Inoculated Control | 0 |
| Inoculated Control | 100 |
| Inoculated 1 oz. AuxF06 | 15 |
| Inoculated 2 oz. AuxF06 | 4 |
| Inoculated 16 oz. Benlate ® | 68 |
| Inoculated 4 oz. Benlate ® | 85 |

Figure 2:
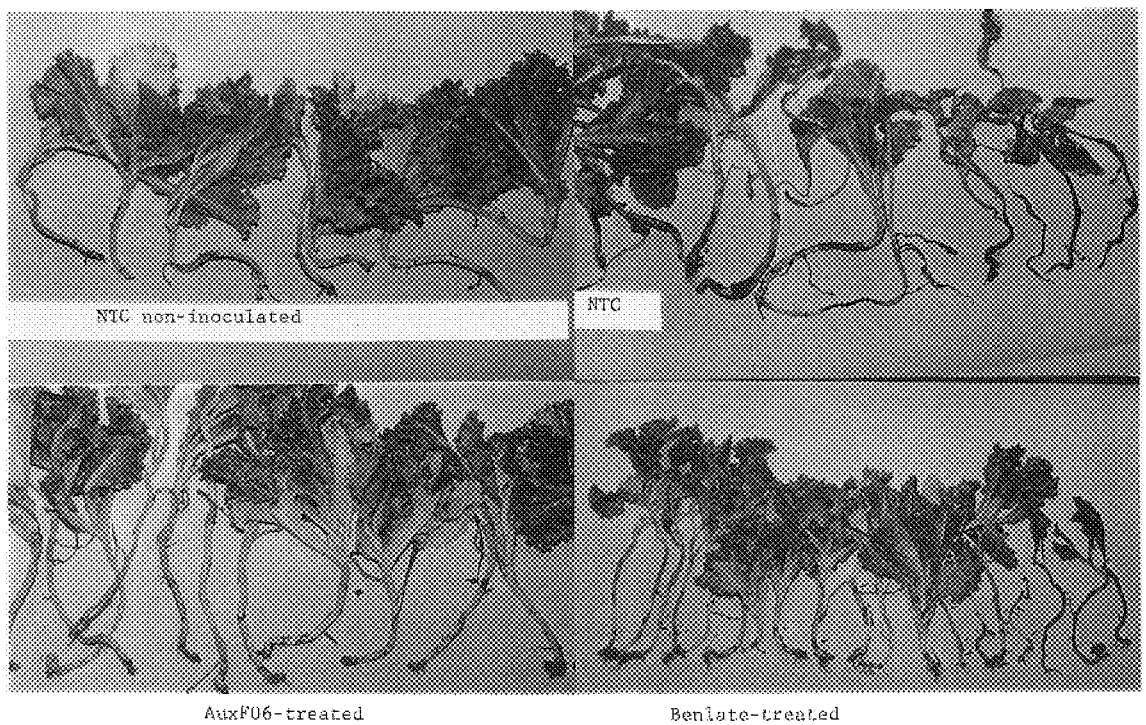
FIG. 2 depicts the effect of AuxF06 on resistance of lettuce plants to fungal infection. Top left panel: control non-inoculated cabbage plants; Top right panel: cabbage plants inoculated with Botrytis; Bottom left panel: cabbage plants treated with 2 oz/A (141 g/ha) AuxF06 and inoculated with Botrytis; Bottom right panel: cabbage plants treated with 16 oz/A (1.1 kg/ha) Benlate® and inoculated with Botrytis.

FIG. 2 shows representative plants from the treatments in Table 10. The discolored lesions on the stems of the infected plants indicate the severity of fungal infection. The non-treated control (NTC) that was not inoculated with Botrytis showed no signs of infection. Lettuce treated with the mixture of glutamic acid and glycolic acid (AuxF06) resisted infection much more successfully.

EXAMPLE 10

The value of the present invention in protecting plants from drought stress was investigated in a greenhouse experiment with Heads-Up Cabbage. Heads-Up cabbage seed (lot #79739-9c, 92% germ 9-97) was purchased from Harris Seeds Inc. and planted in 6×12 well plug flats. Seedlings were transplanted at the one-true-leaf stage into half-gallon pots at 2 per pot. Plants received the first spray treatment at approximately 2.5 mL per plant when they had reached an average of 7 true-leaves per plant. The second treatment was applied 5 days later, just following the final watering of the plants to be drought treated. The soil moisture content was measured at drought initiation. A plotting of the soil moisture points gave a nearly perfect "Normal" distribution pattern. The drought treatment was performed by withholding water until a severe wilt was apparent, but without passing the permanent wilting point. At 7 days following drought initiation, pots were watered, terminating the drought treatment. At 24 hr following drought termination the plants were harvested. Fresh and dry weights of all plants were measured.

Figure 3:
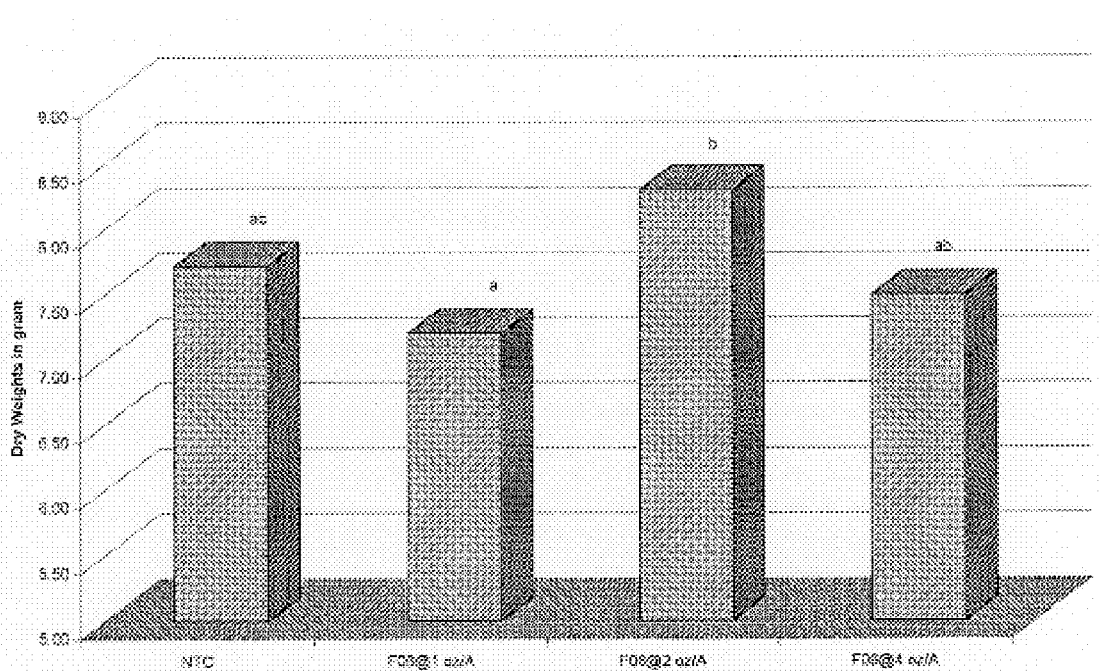
FIG. 3 depicts a bar graph showing the dry weight of cabbage plants after being treated with AuxF06. The top panel represents cabbage plants that were well watered (i.e., not subject to drought conditions) and the bottom panel represents cabbage plants that were drought-stressed and subsequently rehydrated. The bars in each panel, from left to right, represent a non-treated control, treatment with AuxF06 at 1 oz/A (71 g/ha), treatment with AuxF06 at 2 oz/A (141 g/ha) and treatment with AuxF06 at 4 oz/A (282 g/ha). The bottom panel represents cabbage plants that were drought-stressed.
Figure 3:
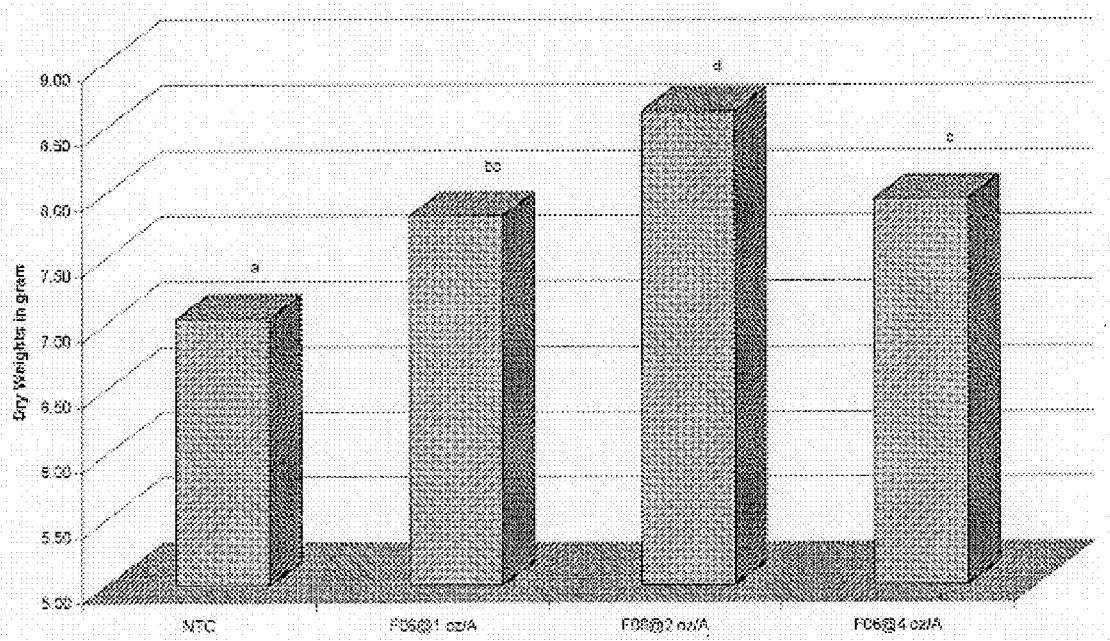

The results are shown in the bar graph in FIG. 3. As a result of the drought treatment, non-treated control plants weighed an average 7.0 g or about 10% less than the average weight of well-watered plants not subjected to the drought treatment, which weighed an average 7.8 g. In spite of the drought treatment, the cabbage plants treated with the composition of the invention (designated "F06" in the figure) had increased in weight. The letters above each bar on the graph denotes statistical significance. Statistical analysis of the results shows that, although the most effective rate of F06 (2 oz/A) (141 g/hectare) increased cabbage weight of well watered plants by 6.4% the difference was not significant. When plants were drought stressed the comparable increase in weight was 2.9% and highly significant. Plants treated with F06 at 1 oz/A (71 g/ha) and 4 oz/A (282 g/ha) were also significantly heavier than controls following drought stress. These results demonstrate the effectiveness of the present invention in preventing loss of agricultural yields due to drought stress.

EXAMPLE 11

The effect of the composition of this invention on seed germination was studied in a petri dish experiment. A single Whatman (Maidstone, UK) 90 mm filter paper was placed in each petri dish and 5 ml of treatment solution were added to the dish. 130 seeds of Kentucky Blue Grass were then added to each dish. After 6 days, the number of seeds germinated in each petri dish was counted and results shown below in Table 11.

TABLE 11

Kentucky Blue Grass seed germination study in petri dishes

| Treatments | # germinated Seeds, avg. per petri dish | % increase from control |
| --- | --- | --- |
| Control | 12.3 ± 2.5 | 100 |
| GLU/GA 100 ppm | 32.0 ± 2.4 | 260 |
| GLU/GA 10 ppm | 16.0 ± 2.2 | 130 |
| GLU/GA 1 ppm | 14.7 ± 2.1 | 120 |
| GLU/GA 0.1 ppm | 15.7 ± 1.2 | 127 |

Results show that the treatment containing 100 ppm w/v of the glutamic/glycolic acid solution increased germination 260% over controls. The glycolic acid used in this experiment was crystalline GlypureTm from DuPont.

EXAMPLE 12

Figure 4:
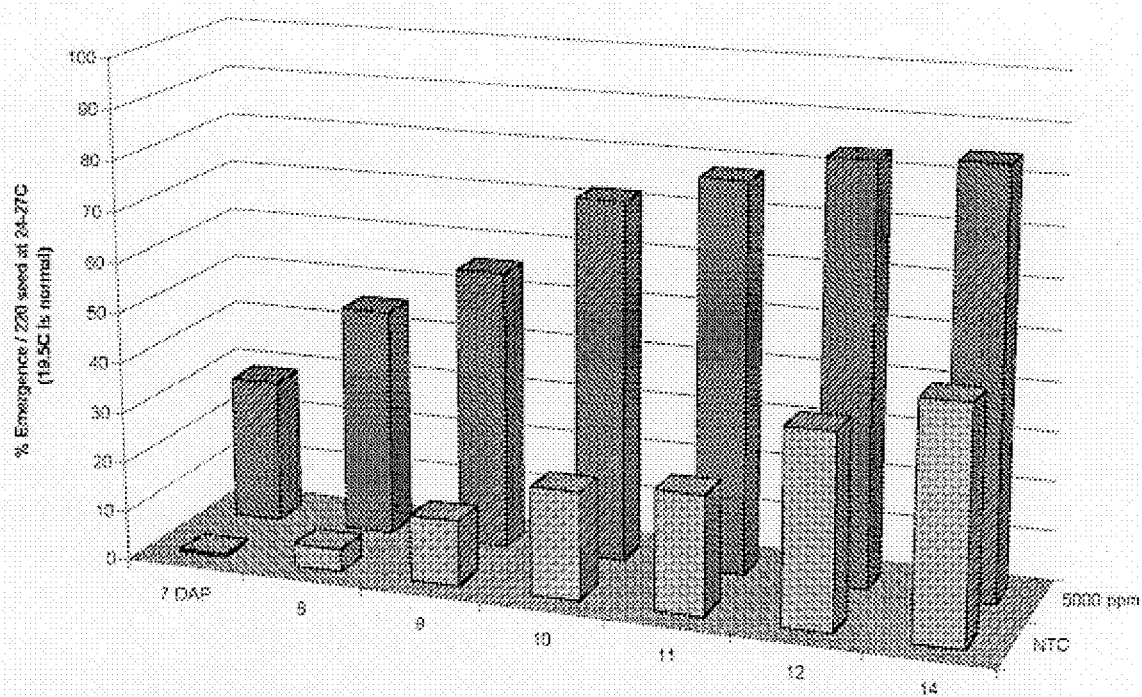
FIG. 4 depicts a bar graph showing the percentage of germinated petunia seeds coated with AuxF06 as a function of the number of days after planting (DAP). Bars in the foreground represent non-treated controls (NTC) whereas bars in the background represent germinated petunias after being treated with 5,000 ppm AuxF06.

The glutamic acid/glycolic acid composition used in the previous example was mixed with polyvinyl-pyrrolidone (Sigma Chemicals, St. Louis, Miss.) to form a mixture that was used to coat seeds. Seeds are often commercially coated with pesticides and other agents to increase the viability of germinated seedlings. In this experiment, a coating solution was made from a solution containing 5,000 ppm w/v glutamic acid/glycolic acid with 24 g polyvinyl-pyrrolidone. The mixture was used to coat petunia seeds (Ultra Red Star, Goldsmith Seed, Gilray, Calif.) in the manner described below: Approximately 1000 petunia seeds were placed in a small dish and 2–3 ml of the coating solution was poured over the seeds. Seeds were agitated with the mixture until all were coated (2–4 minutes). The seed suspension was then poured onto an absorbent surface to remove the excess fluid. After a few minutes, seeds were removed and air-dried. The dried seeds and non-coated control seeds were planted in a seedling planting mix and the number of germinated seedlings counted at different days after planting (DAP). Results are shown below in the bar graph (FIG. 4). AuxF06 is the company designation of the glutamic acid/glycolic acid mixture. The results show that seeds coated with the composition of this invention germinated much faster than control seeds. A week after seeds had been planted, none of the untreated seeds had germinated whereas, at this time, over 35% of the treated seeds had germinated. Two weeks after planting, more than twice as many of the coated seeds had germinated than had controls.

EXAMPLE 13

A cotton seed sample (Fibermax 832) was received from a Georgia cotton farmer which was fungicide coated (blue).

A coating solution was created from 200 ml F06 at 5000 ppm with 24 g polyvinyl-pyrrolidone (molecular weight= 10,000, PVP-10). Approximately 200 cotton seeds were poured into a small weigh-boat. Coating solution was poured over the seeds to submersion. The solution was mixed until all seed was wetted (2–4 min). The coating solution was then poured off and the seed spread out onto an absorbent surface and allowed to dry. The control was only treated with the fungicide, not F06.

The following day (>12 hr later) control and coated seed was planted 1 inch subsurface in seedling planting mix. Placement was 1 seed/well in 6×12 well flats. Results are shown in FIG. 5.

Figure 5:
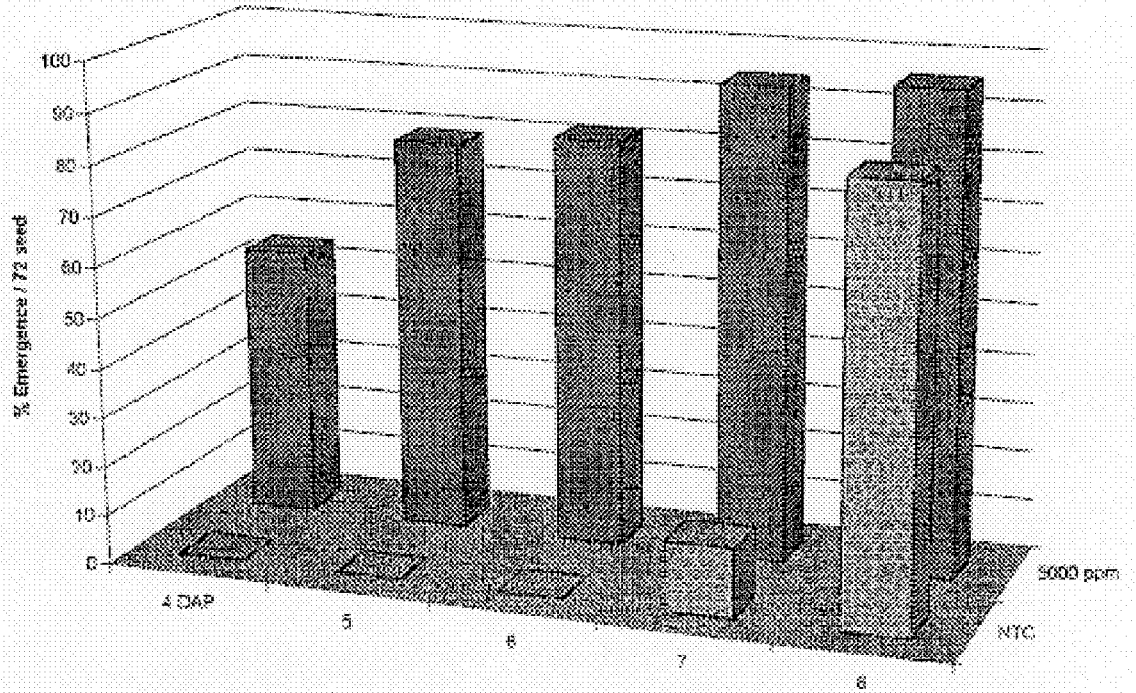
FIG. 5 depicts a bar graph showing the percentage of germinated cotton seeds coated with an AuxF06/polyvinyl pyrrolidone solution as a function of the number of days after planting. Bars in the foreground represent non-treated controls (NTC) whereas bars in the background represent seeds treated with 5,000 ppm AuxF06.

FIG. 5 shows that seeds coated with AuxF06 in combination with the fungicide polyvinyl-pyrrolidone germinated faster than control seeds. A week after seed had been planted, only about 10% of the non-treated control seed had germinated, whereas over 90% of the treated seeds had germinated.

While the invention has been illustrated and described in detail in the forgoing description, the same is to be considered as illustrative and not restrictive in character, it being understood that only the preferred embodiments have been shown and described, and that all changes and modifications that come within the spirit of the invention are desired to be protected.

What is claimed is:

1. An agricultural composition comprising glutamic acid and glycolic acid.

2. The composition of claim 1, wherein said glutamic acid and said glycolic acid are present in amounts effective in increasing plant productivity.

3. The composition of claim 1, wherein said composition is in a carrier medium.

4. The composition of claim 3, wherein said carrier medium is a pesticide.

5. The composition of claim 3, wherein said carrier medium is a fungicide.

6. The composition of claim 3, wherein said carrier medium is water.

7. The composition of claim 1, said composition further comprising a calcium salt.

8. The composition of claim 7, wherein said calcium salt is calcium nitrate.

9. The composition of claim 1, wherein said composition comprises about 0.5 ppm to about 2,500 ppm glutamic acid, and about 0.5 ppm to about 2,500 ppm glycolic acid, all on a weight/volume basis.

10. A composition comprising glutamic acid and a polyglycolic acid having the following formula:

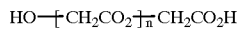

wherein n=1–10.

11. The composition of claim 10, wherein said composition comprises about 0.5 ppm to about 2500 ppm glutamic acid, and about 0.5 ppm to about 2,500 ppm polyglycolic acid, all on a weight/volume basis.

12. The composition of claim 10, wherein said composition is in a carrier medium.

13. The composition of claim 12, wherein said carrier medium is water.

14. The composition of claim 12, wherein said carrier medium is a pesticide.

15. The composition of claim 10, said composition further comprising a calcium salt.

16. The composition of claim 15 wherein said calcium salt is calcium nitrate.

17. A method of treating a plant comprising treating the plant with a composition comprising glutamic acid and glycolic acid.

18. The method of claim 17, wherein said composition comprises about 0.5 ppm to about 2,500 ppm glutamic acid and about 0.5 ppm to about 2,500 ppm glycolic acid, all on a weight/volume basis.

19. The method of claim 17, wherein said composition is in a carrier medium.

20. The method of claim 19, wherein said carrier medium is water.

21. The method of claim 19, wherein said carrier medium is a pesticide.

22. The method of claim 17, wherein the composition further comprises a calcium salt.

23. The method of claim 22, wherein said calcium salt is calcium nitrate.

24. The method of claim 23, wherein said composition comprises about 0.5 ppm to about 2,500 ppm glutamic acid, about 0.5 ppm to about 2,500 ppm glycolic acid and about 100 ppm to about 10,000 ppm calcium nitrate.

25. The method of claim 17, which further comprises treating the plant with an amount of the composition effective to increase plant productivity.

26. The method of claim 17, wherein said plant yields harvestable produce.

27. The method of claim 26, wherein said composition is applied to the plant in amounts effective to increase early ripening of the fruit.

28. The method of claim 17, wherein said composition is applied to the plant in amounts effective to increase the growth of said plant.

29. The method of claim 17, wherein said composition is applied to the plant in the amounts effective to increase plant resistance to environmental stresses.

30. The method of claim 29, wherein said environmental stress is drought stress.

31. The method of claim 17, wherein said composition is applied to the plant in amounts effective to increase the resistance of said plants to disease.

32. The method of claim 17, wherein said composition is applied to seeds of said plant in amounts effective to stimulate seed germination.

33. A method of treating a plant comprising treating the plant with a composition comprising glutamic acid and polyglycolic acid having the following formula:

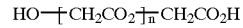

wherein n=1–10.

34. The method of claim 33, said composition further comprising a calcium salt.

35. The method of claim 34, wherein said calcium salt is calcium nitrate.

36. The method of claim 35, wherein said composition further comprises about 100 ppm to about 10,000 ppm of said calcium nitrate.

37. The method of claim 33, wherein said composition is in a carrier medium.

38. The method of claim 33, and which comprises treating the plant with an amount of the composition effective to increase plant productivity.

39. The method of claim 33, wherein said composition comprises about 0.5 ppm to about 2,500 ppm glutamic acid and about 0.5 ppm to about 2,500 ppm of polyglycolic acid.

40. The method of claim 33, wherein said composition is applied to seeds of said plant in amounts effective to stimulate seed germination.

41. The composition of claim 1, said composition consisting essentially of glutamic acid and glycolic acid.

42. A composition consisting essentially of glutamic acid, glycolic acid and a calcium salt.

43. The composition of claim 42, wherein said calcium salt is calcium nitrate.

44. A composition comprising glutamic acid, glycolic acid and at least one carrier medium selected from the group consisting of a fertilizer and a pesticide.

45. The composition of claim 44, wherein said pesticide is a fungicide.

* * * * *